US008101822B2

(12) United States Patent
Li

(10) Patent No.: US 8,101,822 B2
(45) Date of Patent: Jan. 24, 2012

(54) METHOD FOR PREVENTING MUTATION OF PATHOGENS EXPOSED TO TRANSGENIC PLANTS

(76) Inventor: Xiaofang Li, Guangzhou (CN)

( * ) Notice: Subject to any disclaimer, the term of this patent is extended or adjusted under 35 U.S.C. 154(b) by 598 days.

(21) Appl. No.: 12/235,658

(22) Filed: Sep. 23, 2008

(65) Prior Publication Data

US 2009/0083881 A1 Mar. 26, 2009

(30) Foreign Application Priority Data

Sep. 24, 2007 (CN) .......................... 2007 1 0030494

(51) Int. Cl.
*A01H 1/00* (2006.01)
*A01H 5/00* (2006.01)
*C12N 15/09* (2006.01)
*C12N 15/82* (2006.01)

(52) U.S. Cl. ........ 800/279; 800/278; 800/298; 800/260; 800/320.1; 800/314; 800/317.3; 800/317.4; 800/320.2; 435/468

(58) Field of Classification Search ........................ None
See application file for complete search history.

(56) References Cited

FOREIGN PATENT DOCUMENTS

WO WO 2005094340 * 10/2005

* cited by examiner

*Primary Examiner* — Medina A Ibrahim
(74) *Attorney, Agent, or Firm* — Matthias Scholl P.C.; Matthias Scholl

(57) ABSTRACT

A method for preventing mutation of pathogens or pest insects due to exposure to genetically-modified or transgenic plants, comprising: (a) introducing separately a plurality of resistance genes conferring pest and disease resistance to a given recipient plant variety or combinations of the varieties to form a plurality of transgenic plant lines each harboring different resistance genes; (b) multiplying the transgenic plant lines separately to obtain separate transgenic plant lines; and (c) mixing seeds of the separate transgenic plant lines in a specific weight ratio to form a final transgenic product. Additionally, small number of seeds of the non-transformed plants is incorporated in the transgenic plant lines according to demand. As a result, an excessive selective pressure for targeted insects and pathogens are alleviated considerably, the possibility of auto mutation of the targeted insects and pathogens will be reduced, and the application duration of transgenic crop varieties will be prolonged effectively.

8 Claims, No Drawings

METHOD FOR PREVENTING MUTATION OF PATHOGENS EXPOSED TO TRANSGENIC PLANTS

CROSS-REFERENCE TO RELATED APPLICATIONS

This application claims priority benefits to Chinese Patent Application No. 200710030494.8 filed Sep. 24, 2007, the contents of which are incorporated herein by reference.

BACKGROUND OF THE INVENTION

1. Field of the Invention

The invention relates to a method for preventing pathogens from mutating caused by overexpression of transgenes in genetically-modified or transgenic plants.

2. Description of the Related Art

Agriculture relies on a comprehensive and complicated equilibrium, which when disturbed has often unintended effects. For example, it is well-known that excessive application of pesticides to crops results in pesticide resistance of pest and pathogens, i.e., the adaptation of pest and pathogen species targeted by a pesticide resulting in decreased susceptibility to the pesticides applied. In other words, pests develop a resistance to the applied pesticide through artificial selection; after they are exposed to a pesticide for a prolonged period it no longer kills them as effectively. The most resistant organisms are the ones to survive and pass on their genetic traits to their offspring. Similar to pesticide resistance is the phenomenon of transgenic resistance, wherein pests and pathogens become resistant via mutation pathways to transgenic plants and toxins overexcreted by transgenic plants.

It is estimated that the cost of creating pathogen-resistant transgenic crop varieties is at least several hundred thousand dollars per variety. Even so, the high cost does not guarantee predictability. In addition, resistance genes with unusually high intensity will put great specific selection pressure on targeted insects or microbes and will usually lead to endogenous mutation of those organisms. Consequently, the plants will lose their resistance or they will be infested by new pests and diseases. In such cases, new genes have to be discovered and cloned all over.

According to a report in China Science Times, transgenic Bt cotton once displayed good resistance in the field, particularly in the first 3 years of production, but subsequently, the effect began to decline or was even reversed. In the fourth year, the production cost was increased threefold and farmer's income was reduced by 8%. After having been planted consecutively for 7 years, the Bt cotton was plagued by other new insects. As pesticide application had to be increased and the cost of seeds was increased compared to non-transgenic varieties, the income of farmers was reduced.

Prolonging the application duration of transgenic plants and preventing pests and pathogens from mutation caused by them have become a key and unavoidable problem in the field of transgenic engineering. Horizontal resistance in transgenic plants can be obtained via the plants own diversified sources of transgenes. Such resistance would not exert specific selection pressure on pests and pathogens. Plants could display resistance to any possible pests and diseases and may prevent the rampancy of a certain pests and diseases. Thus, resistance duration of transgenic plants can be prolonged greatly and this will benefit the sustainable development of agriculture. Up to now, the bio-safety of gene transfer technology has not been fully confirmed. Enormous and unpredictable risks and threats cannot be excluded for the promoters of transgenes, the expression of foreign genes and possible escape of transgenes. If those cases really happen, large losses for the entire industry and great social consequences may occur.

SUMMARY OF THE INVENTION

In view of the above-described problems, it is one objective of the invention to provide a method for preventing pathogens from mutation caused by genetically-modified or transgenic plants.

To achieve the above objectives, in accordance with one embodiment of the invention, provided is a method for preventing pest insects and pathogens from mutation comprising: introducing separately various genes of interest with pest and disease resistance into given recipient varieties or combinations of the varieties to form various transgenic plant lines harbouring different resistance genes, multiplying the transgenic plant lines separately and mixing seeds of the transgenic plant lines in a specific ratio so as to obtain final product for release in the production. In some cases, a small number of seeds of non-transformed plants can be added in the seeds of the transgenic plant lines.

DETAILED DESCRIPTION OF THE EMBODIMENTS

Individual plant lines with approximately identical phenotypes are adopted as recipients of transgenes in the transformation. Meanwhile, the transgenes originate from various sources of diversified genes of interest. Each plant line is transformed with a separate gene of interest, and those resultant transformed plant lines are mixed in a specific ratio to form a mixed transgenic crop variety and are finally put into production.

Optionally, small amount of seeds of non-transformed plant line are incorporated in the transformed variety in some cases. Without wishing to be bound by theory, in this way, one transgenic plant line provides an asylum of the targeted insects and pathogens for another transgenic plant line and all transgenic plant lines offer asylums for each other. As a result, the selective pressures for the targeted insects and pathogens are alleviated considerably, the possibility of auto mutation of the targeted insects and pathogens will be reduced and the life span of transgenic crop varieties is prolonged effectively.

Although the examples to follow describe experiments performed with certain particular crop plants, the invention relates without limitation to other crop plants besides rice, corn, tobacco and tomato. It also relates to genes of interest with pest and disease resistance, including but not limited to wbph2, Cry IA, Cry I A(b), Cry IA(c), Cry(b), Cry(c), Bt (above seven genes relate to insect resistance), Xa-21 (bacterial resistance), Pi-b, Pi-ta (two fungal resistance genes), CMV-CP (viral resistance).

The term "pathogens," as used herein, refers to biological agents that cause disease or illness to its host. The term is intended to encompass not only bacteria, viruses, protozoa, but also parasites and parasitoids, such as, for example, insects.

EXAMPLES

Example 1

Yue-Xiu-Zhan is used as a recipient variety of rice. The genes wbph2 and Xa-21 with respective resistance to white-backed planthoppers and bacterial leaf blight are introduced into the recipient variety by transformation. After transgenic plants harbouring wbph2 and Xa-21 are produced separately, two stable transgenic plant lines, which are holistically consistent in agronomical traits, are developed via pedigree selection. These two lines are multiplied separately, and their seeds are then mixed in an equal ratio to form the final product for release in production.

Example 2

Feng-Ai-Zhan is used as a recipient variety of rice. Genes of wbph2 and Xa-21 with respective resistance to white-backed planthoppers and bacterial leaf blight are introduced into the recipient variety by transformation. After transgenic plants harbouring wbph2 and Xa-21 are produced separately, two stable transgenic plant lines, which are holistically consistent in agronomical traits, are developed via pedigree selection. These two lines are multiplied separately, and their seeds are then mixed in a weight ratio of transgenic plants harbouring wbph2 to transgenic plants harbouring Xa-21 of 1 to 2 to form the final product for release in production.

Example 3

Yue-Xiang-Zhan is used as a recipient variety of rice. Genes of Pi-b and Pi-ta with respective resistance to different stains of rice blast and gene of Xa-21 with resistance to bacterial leaf blight are introduced into the recipient variety by transformation. After transgenic plants comprising Pi-b, Pi-ta and Xa-21 are produced separately, three stable transgenic plant lines, which are holistically consistent in agronomical traits, are developed via pedigree selection. These three lines are multiplied separately, and their seeds are then mixed in an equal weight ratio. Finally, 1% of the total number of seeds from the non-transformed plants is added to form the final product for release in production.

Example 4

Yue-Feng-Zhan is used as a recipient variety of rice. Genes of Pi-b and Pi-ta with respective resistance to different stains of rice blast and gene of Xa-21 with resistance to bacterial leaf blight are introduced into the recipient variety by transformation. After transgenic plants comprising Pi-b, Pi-ta and Xa-21 separately are produced, three stable transgenic plant lines, which are holistically consistent in agronomical traits, are developed via pedigree selection. These three lines are multiplied separately, and their seeds are then mixed in a weight ratio of 1:3:1 (Pi-b to Pi-ta to Xa-21). Finally, 1% of the total number of seeds from the non-transformed plants is added to form the final product for release in production.

Example 5

KD 19 is used as a recipient variety of cotton. Genes of Cry IA, Cry IA (b), Cry IA (c), Cry (b), and Cry (c) with respective resistance to biotypes of pest insects are introduced into the recipient variety by transformation. After transgenic plants comprising Cry IA, Cry IA (b), Cry IA (c), Cry (b), Cry (c) separately are produced, five stable transgenic plant lines, which are holistically consistent in agronomical traits, are developed via pedigree selection. These five lines are multiplied separately, and their seeds are then mixed in an equal weight ratio. Finally, 0.5% of the total number of seeds from the non-transformed plants is added to form the final product for release in the production.

Example 6

Corn varieties are used as a recipient of transformation. Genes of Cry IA, Cry I A (b), Cry IA (c), Cry (b), Cry (c) with respective resistance to biotypes of pest insects are introduced into the recipient variety by transformation. After transgenic plants comprising Cry IA, Cry IA (b), Cry IA (c), Cry (b), Cry (c) separately are produced, five stable transgenic plant lines, which are holistically consistent in agronomical traits, are developed via pedigree selection. These five lines are multiplied separately, and their seeds are then mixed in a weight ratio of 3:3:2:1:1 (Cry IA to Cry IA (b) to Cry IA (c) to Cry (b) to Cry (c)). Finally, 1% of the total number of seeds from the non-transformed plants is added to form the final product for release in production.

Example 7

Tobacco varieties are used as a recipient of transformation. Insect resistant genes of Cry IA—resistant to tobacco hawk moths, Cry IA (b)—resistant to the tobacco hawk moths, and Cry IA (c)—resistant to an oriental tobacco budworm (*Helicoverpa assulta*) are introduced into the recipient variety by transformation. After transgenic plants comprising Cry IA, Cry IA (b), and Cry IA (c) are produced separately, three stable transgenic plant lines, which are holistically consistent in agronomical traits, are developed via pedigree selection. These three lines are multiplied separately, and their seeds are then mixed in a weight ratio of 1:1:2 (Cry IA to Cry IA (b) to Cry IA (c)). Finally, 0.1% of the total number of seeds from the non-transformed plants is added to form the final product for release in production.

Example 8

Tobacco varieties are used as a recipient of transformation. Insect resistant genes of Cry IA—resistant to tobacco hawk moths, Cry IA (b)—resistant to the tobacco hawk moths, and Cry IA (c)—resistant to oriental tobacco budworm (*Helicoverpa assulta*) are introduced into the recipient variety by transformation. After transgenic plants comprising Cry IA, Cry IA (b), Cry IA (c) separately are produced, three stable transgenic plant lines, which are holistically consistent in agronomical traits, are developed via pedigree selection. These three lines are multiplied separately, and their seeds are then mixed in a weight ratio of 3:1:1 (Cry IA to Cry IA (b) to Cry IA (c)). Finally, 0.2% of the total number of seeds from the non-transformed plants is added to form the final product for release in production.

Example 9

Tomato varieties are used as a recipient of transformation. Resistance genes of Cry IA (b)—resistant to Lepidoptera insects, Bt—resistant to tomato fruit pests and boring moths, and Bt+CMV-CP—resistant to viral diseases are introduced into the recipient variety by transformation. After transgenic plants comprising Cry I A (b), Bt, and Bt+CMV-CP separately are produced, three stable transgenic plant lines, which are holistically consistent in agronomical traits, are developed via pedigree selection. These three lines are multiplied separately, and their seeds are then mixed in a weight ratio of 1:3:1 (Cry I A (b) to Bt to Bt+CMV-CP). Finally, 0.5% of the total number of seeds from the non-transformed plants is added to form the final product for release in production.

Example 10

Tomato varieties are used as a recipient of transformation. Resistance genes of Cry IA (b)—resistant to Lepidoptera insects, Bt—resistant to tomato fruit pests and boring moths, and Bt+CMV-CP—resistant to viral diseases are introduced into the recipient variety by transformation. After transgenic plants comprising Cry I A (b), Bt, Bt+CMV-CP separately are produced, three stable transgenic plant lines, which are holistically consistent in agronomical traits, are developed via pedigree selection. These three lines are multiplied separately, and their seeds are then mixed in a weight ratio of 1:1:1. Finally, 1% of the total number of seeds from the non-transformed plants is added to form the final product for release in production.

Example 11

Tomato varieties are used as a recipient of transformation. Resistance genes of Cry IA (b)—resistant to Lepidoptera insects, Bt—resistant to tomato fruit pests and boring moths, and Bt+CMV-CP—resistant to viral diseases are introduced into the recipient variety by transformation. After transgenic plants comprising Cry I A (b), Bt, Bt+CMV-CP separately are produced, three stable transgenic plant lines, which are holistically consistent in agronomical traits, are developed via pedigree selection. These three lines are multiplied separately, and their seeds are then mixed in a weight ratio of 3:2:1 (Cry I A (b) to Bt to Bt+CMV-CP) to form the final product for release in production.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preventing mutation of pathogens caused or accelerated by exposure to genetically-modified or transgenic plants, comprising:

(a) introducing separately more than two resistance genes conferring pest and disease resistance to a given recipient plant variety or combinations of said varieties to form more than two transgenic plant lines each harboring different resistance genes;

(b) multiplying said transgenic plant lines separately to obtain separate transgenic plant lines; and (c) mixing seeds of said separate transgenic plant lines with seeds of non-transformed plants in a specific weight ratio to form a final transgenic product.

2. A method for preventing mutation of pathogens caused or accelerated by exposure to genetically-modified or transgenic plants, comprising: (a) introducing separately a plurality of resistance genes conferring pest and disease resistance to a given recipient plant variety or combinations of said varieties to form a plurality of transgenic plant lines each harboring different resistance genes; (b) multiplying said transgenic plant lines separately to obtain separate transgenic plant lines; and (c) mixing seeds of said separate transgenic plant lines with seeds of non-transformed plant lines in a specific weight ratio to form a final transgenic product; wherein said genetically-modified or transgenic plants are selected from the group consisting of rice, corn, cotton, tobacco, or tomato; and wherein said resistance genes are selected from the group consisting of wbph2, Pi-b, Pi-ta, Xa-21, Cry IA, Cry IA (b), Cry IA (c), Bt and Bt+CMV-CP.

3. The method of claim 1, wherein said resistance genes are introduced into different individuals of said recipient varieties.

4. The method of claim 1, wherein said final transgenic product is a mixture of said various transgenic plant lines harboring said various resistance genes and said non-transformed plants.

5. The method of claim 2, wherein the pathogens are selected from the group consisting of white-backed planthoppers, tobacco hawk moths, oriental tobacco budworms, Lepidoptera insects, tomato fruit pests, boring moths, viruses and pathogens that cause rice blast and leaf blight diseases.

6. The method of claim 2, wherein said genetically-modified or transgenic plants are rice; the resistance genes are selected from the group consisting of wbph2 gene, Pi-b gene, Pi-ta gene, and Xa-21 gene; and the pathogens are white-backed plant hoppers and pathogens that cause rice blast and leaf blight diseases.

7. The method of claim 2, wherein said genetically-modified or transgenic plants are tobacco; the pest resistance genes are selected from the group consisting of Cry IA, Cry IA (b), Cry IA (c), Cry (b), and Cry (c); and the pathogens are selected from the group consisting of tobacco hawk moths and oriental tobacco budworms.

8. The method of claim 2, wherein said genetically-modified or transgenic plants are tomato; the pest resistance genes are selected from the group consisting of Cry IA (b), Bt and Bt+CMV-CP; and the pathogens are selected from the group consisting of Lepidoptera insects, tomato fruit pests, boring moths, and virus.

* * * * *